US00PP33777P2

(12) United States Plant Patent
Korlipara

(10) Patent No.: US PP33,777 P2
(45) Date of Patent: Dec. 21, 2021

(54) ***BRUNNERA* PLANT NAMED 'ALEXANDRIA'**

(50) Latin Name: *Brunnera macrophylla*
Varietal Denomination: Alexandria

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 17/164,450

(22) Filed: Feb. 1, 2021

(51) Int. Cl.
*A01H 5/02* (2018.01)
*A01H 6/00* (2018.01)

(52) U.S. Cl.
USPC ..... Plt./412
CPC ..... *A01H 6/00* (2018.05)

(58) Field of Classification Search
USPC ..... Plt./412
CPC ..... A01H 5/02
See application file for complete search history.

(56) References Cited

PUBLICATIONS https://gpnmag.com/news/terra-nova-introduces-new-brunnera/; Jan. 23, 2020; 1 page.*

* cited by examiner

*Primary Examiner* — Kent L Bell
(74) *Attorney, Agent, or Firm* — Klarquist Sparkman, LLP

(57) ABSTRACT

A new and distinct cultivar of *Brunnera* plant characterized by its intense silver-green veiling of the leaves and the very large leaf and plant size.

2 Drawing Sheets

Botanical denomination: *Brunnera macrophylla.*
Variety designation: 'Alexandria'.

BACKGROUND OF THE INVENTION

The present invention relates to a new and distinct cultivar of *Brunnera macrophylla*, given the name, 'Alexandria'. *Brunnera* is in the family Boraginaceae. This new cultivar was bred for large, silver colored leaves and good flowers. This new cultivar is the result of a planned breeding program in Canby, Oreg. The parents were unnamed, unpatented proprietary seedlings. Compared to the pollen parent, 'Alexandria' has larger leaves and shorter petioles. Compared to the seed parent, 'Alexandria' has a smooth silver surface with no breaks in the veiling.

This plant is unique in its combination of intense silver-green veiling of the leaves and the very large leaf and plant size.

Compared to *Brunnera* 'Alexander's Great' (U.S. Plant Pat. No.25,789), the new cultivar is a more vigorous plant, has more intense veiling with no breaks in the veil, resulting in an entirely different look.

Compared to *Brunnera* 'Sea Heart' (U.S. Plant Pat. No. 24,684) and 'Silver Heart' (U.S. Plant Pat. No. 24,685), the new variety is more vigorous, with longer, larger leaves, and becomes a larger plant.

The new variety has been reproduced only by asexual propagation (division and micropropagation). Each of the progeny exhibits identical characteristics to the original plant. Asexual propagation by division and micropropagation as done in Canby, Oreg., shows that the foregoing characteristics and distinctions come true to form and are established and transmitted through succeeding asexual propagations. The present invention has not been evaluated under all possible environmental conditions. The phenotype may vary with variations in environment without a change in the genotype of the plant.

DETAILED PLANT DESCRIPTION

Figure 1:
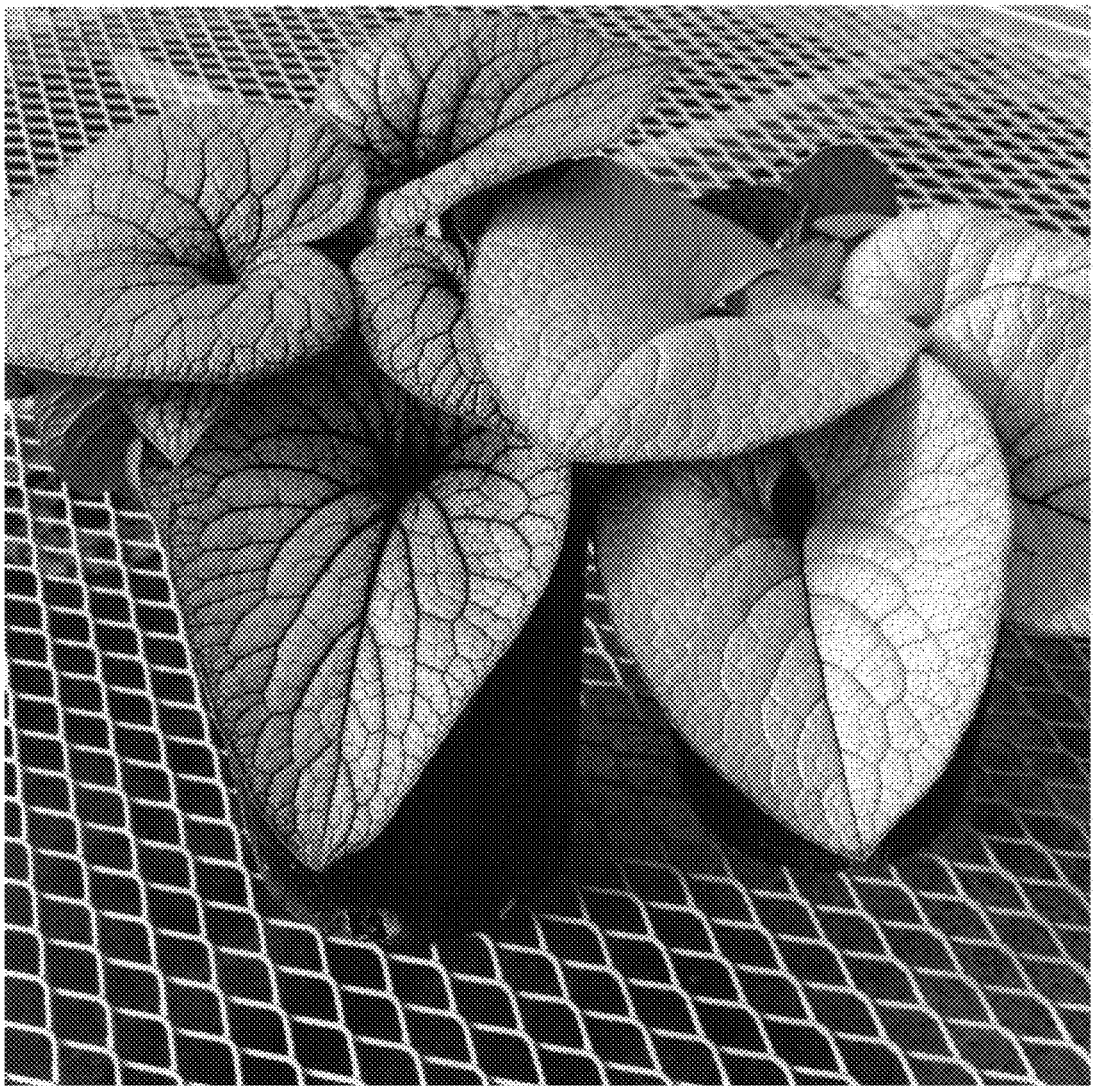
FIG. 1 shows a four-month-old *Brunnera* 'Alexandria' growing in a 4" container (on Right) and *Brunnera* 'Alexander's Great' (on Left) in Canby, Oreg.
Figure 2:
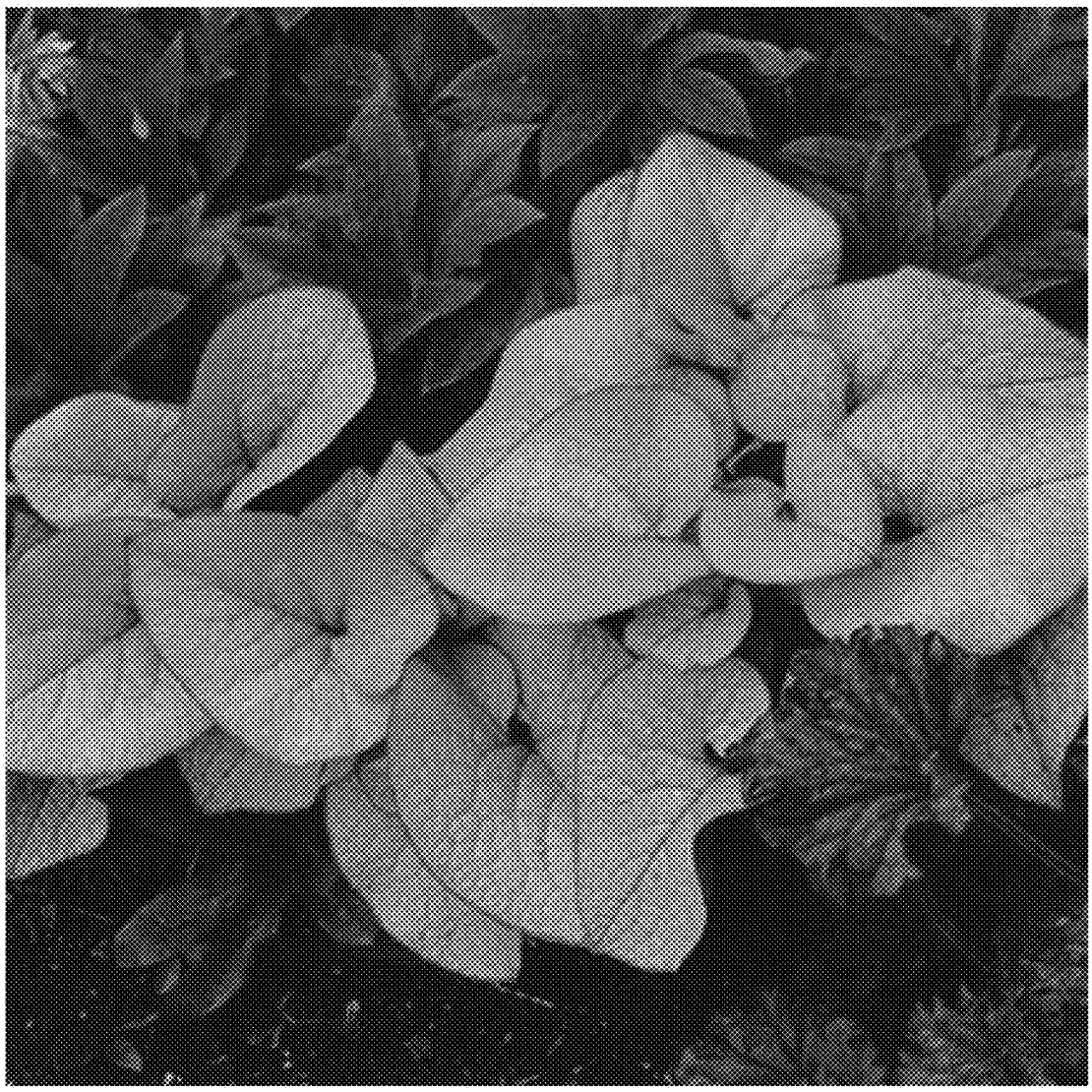
FIG. 2 shows one-year-old *Brunnera* 'Alexandria' plants in a field setting.

The following is a detailed description of the new *Brunnera* cultivar based on observations of a one-year-old specimen in flower grown in an unheated shade house and a six-month old plant in leaf grown in a cool greenhouse in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The data for the flowers are from the first plant and the data for the plant and leaves are from the second plant. The color descriptions are all based on The *Royal Horticultural Society Colour Chart,* 5$^{th}$ edition.

Plant:

*Form.*—Rhizomatous, herbaceous perennial.
*Cold hardiness.*—USDA Zone 3-8.
*Size.*—Grows to 38 cm wide and 16 cm high.
*Habit.*—Compact, mounding.
*Stem.*—Rosette.
*Vigor.*—Excellent.

Leaf:

*Type.*—Simple.
*Arrangement.*—Basal.

*Shape*.—Cordate to ovate.
*Venation*.—Pinnate.
*Margins*.—Entire.
*Apex*.—Acute.
*Base*.—Cordate.
*Blade size*.—Grows to 19 cm long and 15 cm wide.
*Number of leaves per shoot*.—12 to 15.
*Surface texture*.—Coarsely pubescent on both sides.
*Petiole description*.—Grows to 13.5 cm long and 3.5 mm wide, coarsely pubescent, Greyed Purple N186B at base lightening to 147B near blade.
*Leaf color*.—Topside Greyed Green 190C except for veins and margins Green 139A, bottom side between Green 138A and 138B.

Inflorescence:
*Type*.—Terminal panicle.
*Number of flowers*.—105 per panicle.
*Peduncle*.—22 cm tall and 3 mm wide, pubescent, Yellow Green 146C on both sides, with about 13 small petiolate (petioles to 7 mm in length, 2 mm wide, pubescent Green 136B) to sessile leaves, grows to 39 mm long and 2.5 mm wide, ovate, entire, acute at tip, attenuate at base, pubescent with leaf color 190C.
*Pedicel*.—4 mm long, less than 1 mm wide, pubescent, Yellow Green 146C.
*Bloom period*.—May to June in Canby, Oreg.

Flower bud:
*Size*.—1.3 mm wide and 1.4 mm deep.
*Description*.—Orbicular.
*Surface texture*.—Glabrous.
*Color*.—Purple 76A.

Flower:
*Type*.—Regular.
*Shape*.—Rotate.
*Corolla description*.—5 mm wide and 2 mm deep, top side colored Blue Group 101B with a White N155A eye, bottom side Violet Blue 97D; with 5 broadly obovate lobes, each 2 mm wide and 2 mm deep, obtuse, entire, glabrous; tube 1 mm long and 1 mm to 2 mm wide, outside Purple 77B near lobes to Yellow White 158D.
*Sepal description*.—5 in number, 0.75 mm in length, 0.50 mm wide, color both inside and outside is Green 136B, slightly villous.
*Calyx description*.—Campanulate, 1 mm wide and 1 mm deep, 5-lobed, lobes ovate, acute, entire, pubescent outside, glabrous inside.
*Pistil description*.—1, 1 mm long, Yellow Green 144A, ovary 4 lobed and about 0.5 mm long, style and stigma 0.5 mm long.
*Stamen description*.—5, filaments 1 mm long and White 155D, anthers 1 mm long and Black 202A, pollen White 155D.
*Style description*.—Cylindrical, 0.5 mm in length, Yellow Green 145C.
*Stigma description*.—Ovoid, about 0.3 mm long and 0.2 mm wide, Yellow Green 145D.
*Anther description*.—Ovate, about 0.75 mm long and 0.50 mm wide, color NN155A.
*Pollen*.—None seen.
*Fragrance*.—None.
*Lastingness*.—A spike blooms for about 4 weeks on the plant. Individual flowers last 2 to 3 days.

Seed: Nutlets, round, less than 1 mm in size, Brown N200A, averaging 2 per flower if pollinated.

Pests and diseases: *Brunnera* have no major pests or disease problems. This plant has shown no special disease or pest resistance in Canby, Oreg.

I claim:

1. A new and distinct cultivar of *Brunnera* plant substantially as shown and described.

* * * * *